United States Patent [19]
Rosenbaum

[11] Patent Number: 5,971,972
[45] Date of Patent: Oct. 26, 1999

[54] FAILSAFE INTRAVENOUS TRANSFUSION SYSTEM FOR TYPED BLOOD

[76] Inventor: Jay D. Rosenbaum, 9 Eastland Dr., Glen Cove, N.Y. 11542

[21] Appl. No.: 08/883,328

[22] Filed: Jun. 26, 1997

Related U.S. Application Data

[60] Provisional application No. 60/020,789, Jun. 27, 1996.

[51] Int. Cl.⁶ ............................. A61B 19/00; A61M 5/32
[52] U.S. Cl. ............................................................. 604/411
[58] Field of Search ................................... 604/403–414

[56] References Cited

U.S. PATENT DOCUMENTS

| | | |
|---|---|---|
| 3,698,383 | 10/1972 | Baucom . |
| 3,915,212 | 10/1975 | Bujan et al. ............................. 604/408 |
| 4,150,673 | 4/1979 | Watt . |
| 4,650,475 | 3/1987 | Smith et al. ............................. 604/189 |
| 4,678,458 | 7/1987 | Fredeking . |
| 4,804,363 | 2/1989 | Valeri ......................................... 604/6 |
| 4,880,425 | 11/1989 | Kuhlemann et al. .................... 604/404 |
| 5,078,683 | 1/1992 | Sancoff et al. ............................ 604/67 |
| 5,125,920 | 6/1992 | Ishida . |
| 5,180,504 | 1/1993 | Johnson et al. ......................... 210/767 |
| 5,314,421 | 5/1994 | Leuenberger . |
| 5,368,586 | 11/1994 | Van Der Heiden et al. ........... 604/403 |
| 5,595,187 | 1/1997 | Davis ...................................... 128/771 |
| 5,720,729 | 2/1998 | Kriesel .................................... 604/132 |
| 5,769,811 | 6/1998 | Stacey et al. ............................... 604/4 |

FOREIGN PATENT DOCUMENTS

| | | |
|---|---|---|
| 1282046 | 5/1962 | France . |
| 1 358 380 | 7/1974 | United Kingdom . |

*Primary Examiner*—John G. Weiss
*Assistant Examiner*—Ki Yong O
*Attorney, Agent, or Firm*—Richard C. Litman

[57] ABSTRACT

An apparatus and method of its use to prevent accidental transfusion of mismatched blood types from a blood bag containing pre-typed blood to a patient. The system includes two major independent but mating components: 1) a cannula spike attached to a cannula adapted for intravenous infusion of a fluid from the bag into a patient and 2) a plurality of different individual receptacle ports of graduated size, of which at least one is selectively attached to the outside of pilot tube at the time of blood typing. The cannula spike is a connected series of decreasingly sized individual cannula spike units, each unit being configured to be matingly received by and uniquely coded to its matching female receptacle port. Each of the units is individually removable from the cannula spike and the last unit may be affixed permanently to the cannula. Each unit may also be color coded, bar coded, and affixed with linear indicia to assist the user in avoiding an accidental mismatch between blood types.

11 Claims, 6 Drawing Sheets

FAILSAFE INTRAVENOUS TRANSFUSION SYSTEM FOR TYPED BLOOD

CROSS-REFERENCE TO RELATED APPLICATION

This application claims the benefit of U.S. Provisional Patent Application Serial No. 60/020,789, filed Jun. 27, 1996.

BACKGROUND OF THE INVENTION

1. Field of the Invention

The present invention relates to an apparatus to prevent accidental transfusion of mismatched blood types from a blood bag containing pre-typed blood to a patient of a different blood type. More particularly, each of a connected series of decreasingly sized individual cannula spikes is configured to be matingly received by, and uniquely coded to, its unique and matching female receptacle which is permanently attached to the blood bag.

2. Description of the Prior Art

Various inventions are known which have been proposed to help prevent the fatal effect of infusion of an improperly matched blood type to a patient. Each of such inventions have major drawbacks which generally stem from a requirement that the healthcare provider take positive, cognitive actions to avoid an improper match. The prior inventions, although serving to alert or remind the healthcare provider that a mismatch can occur, generally do little to actually physically prevent and actively discourage an incorrect connection between a typed blood bag and a cannulated patient otherwise effected by an unobservant or persistent healthcare provider.

To appreciate the disadvantages of the known art, an understanding of the blood typing system and the elements common to all patient cannulations is necessary. Typically, when blood is donated, the blood is prepared and typed according a universal blood typing system: A, B, AB, and O wherein AB is a universal recipient and O is a universal donor. The rh-factor of blood is also typed as positive (+) or negative (−). Hence, each bag may contain any one of eight different blood types and is so labelled for future use and for cold storage. This critical point provides the first opportunity to modify the blood bag to prevent future mistakes.

When a patient is in need of blood, the patient is also blood typed, and may be labelled too, whether by bracelet or other means. However, not all patients must receive an exactly matched blood type. Some blood types are acceptable to some patients in accordance with the universal blood typing system: AB patients may receive all blood types, AB, A, B or O; A patients may receive A or O type blood; B patients may receive B or O type blood; but, O patients may receive only O. Moreover, mismatched rh-factors (+ instead of −, and vice versa), may be critical to the welfare of the patient, nevertheless, often are not critical. Therefore, an rh-factor mismatch may be voluntarily risked in certain emergency cases, so long as the proper blood type is available and chosen.

Based upon such information, the appropriately labelled blood bag is matched to the patient. Each bag is typically provided with a pilot tube depending from a lowermost edge, which is provided with a puncturable diaphragm. A cannula, typically having a bag end attached to a hollow spike for puncturing the diaphragm and a patient end adapted for venous infusion, is provided as a separate unit which, when inserted into both bag and patient, allows the bag to be hung on an I.V. pole and allow the red blood cells to infuse by gravity into the patient.

When simple labelling techniques are used to identify blood bags, the ease of making a mistake is obvious. By merely misreading a label, the wrong blood bag may be chosen by the health care provider even when both donor blood and recipient patient are correctly typed. Statistics show that this type of accident is the most frequently observed in practice, whereas blood bag labelling mistakes rarely occur during the labelling process itself.

The likelihood of such cognitive mistakes arising is an inherent and major disadvantage of the following devices intended to avoid such mistakes. For example, U.S. Pat. No. 5,314,421 issued May 24, 1994 to Leuenberger describes a microporous plastic film blood pack label which avoids wrinkling and thus distortion of its printed indicia. U.S. Pat. No. 3,698,383 issued Oct. 17, 1972 to Baucom describes combined elements including a patient identification band, having removable labels and a fastener, integrally combined with a pilot tube depending from a blood bag from which the band is ultimately separated. This system is used strictly to cross-identify, by means of printed indicia, a biological fluid and its recipient and fails to provide any physical impediments to mismatching the pilot tube with a patient cannula.

Other devices focus on preventing accidents by use of physical impediments, which do tend to limit the failure of use of cognitive skills which cause accidents. For example, U.S. Pat. No. 4,678,458 issued Jul. 7, 1987 to Fredeking describes an apparatus and method using a lock and key to avoid mistakes during plasmapheresis, which involves taking blood and then returning the red blood cells back to the same donor. The flow of returned blood cells is allowed only by using a unique key to unlock a lock box which controls a roller clamp interposed on a flexible tubing cannula between the blood bag and the donor patient. U.S. Pat. No. 5,125,920 issued Jun. 30, 1992 to Ishida is directed towards the prevention of mislabelling blood component bags at the time of blood donation (rather than towards prevention of misidentifying the bags at transfusion time), by providing several component bags interconnected by tubing for receiving blood. However, an inherent problem with such devices includes the inordinate amount of time necessary to operate the device thus tending to dedicate its use exclusively to autologous circumstances and teaching away from its use in emergency settings.

Figure 5:
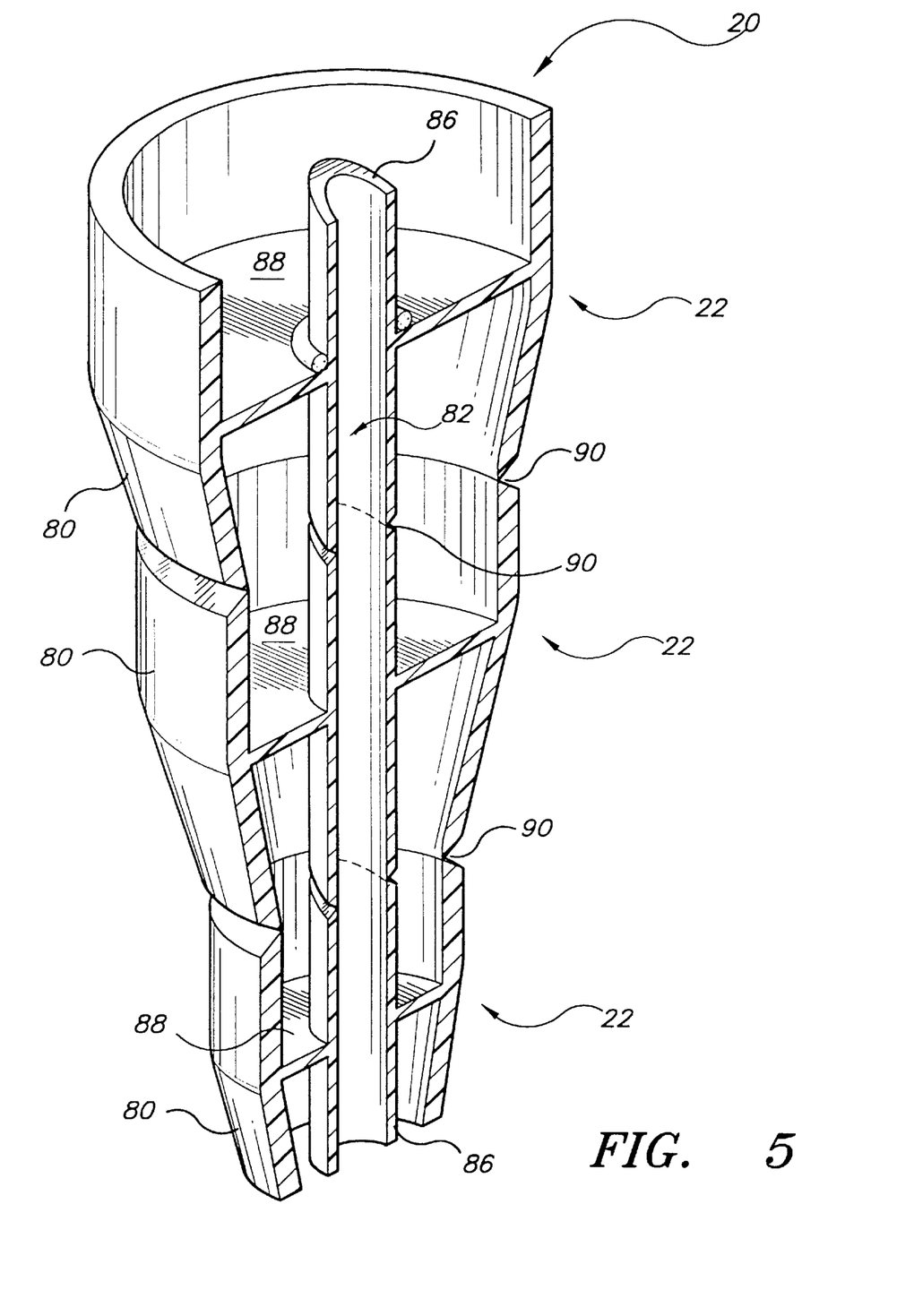
FIG. 5 is a sectional perspective view of the spike component of a third embodiment.
Figure 6:
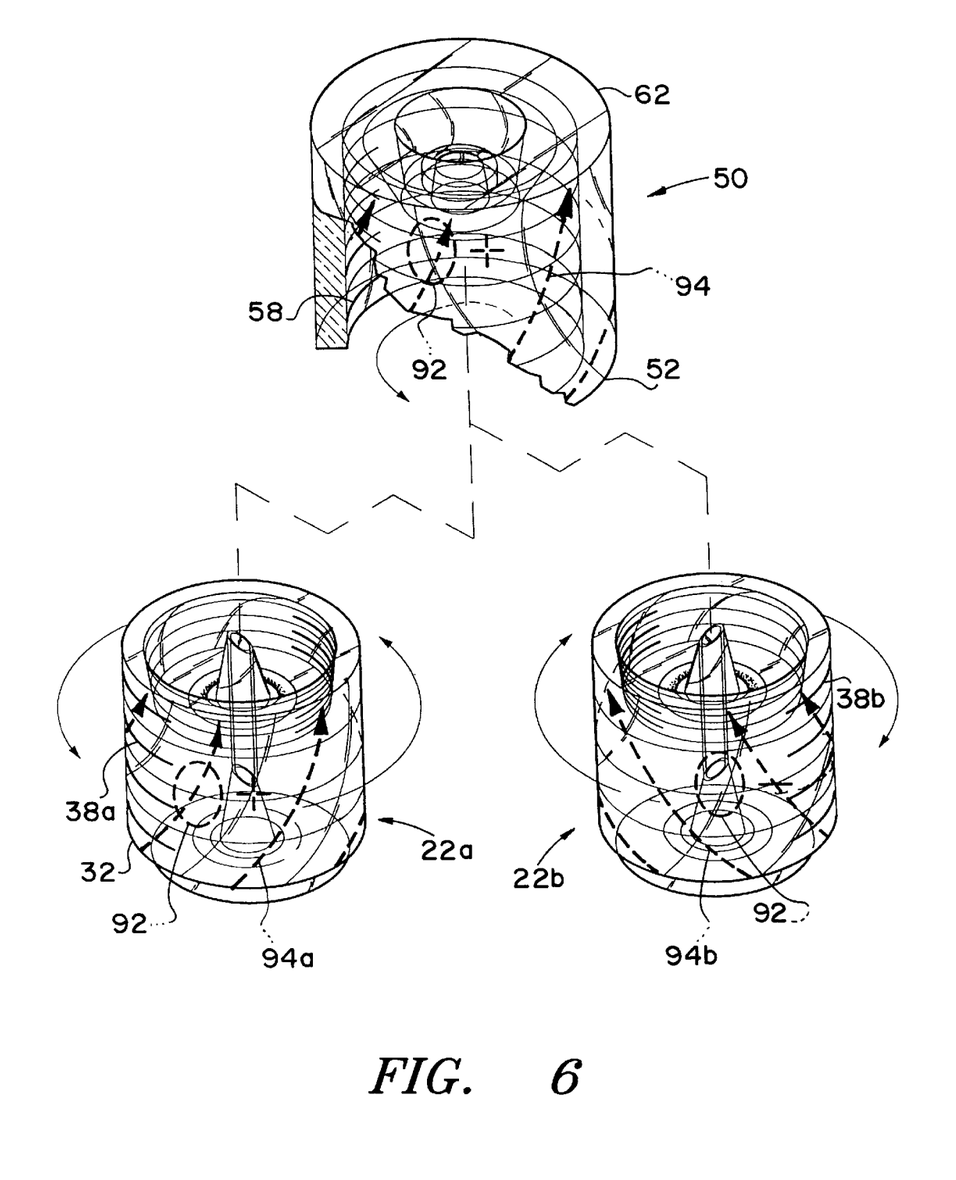
FIG. 6 is a partially fragmented, perspective view of several components of the system having been coded for visual identification of blood type.

Finally, U.S. Pat. No. 4,150,673 issued Apr. 24, 1979 to Watt describes a blood bag having coded inlet-outlet fitments directed at preventing improper transfusions of bag contents. Like a child's peg and hole playset, a series of port fitments attached to the blood bag are coded according to various geometric shapes, which requires that only a correctly shaped hollow spike is allowed into the correctly coded port to permit puncture of the bag and thereby start flow of the fluid contained therein. FIG. 5 and FIG. 6 of the Watt patent show additional embodiments of the fitments and a brief accompanying description suggests that overlay fitments provided as a separate unit can be used to convert a bag having a conventional port to the coded system.

Although the simple Watt system does limit the inadvertent mismatch of ports and spikes of different shapes, it fails to teach the use of any one port as specifically matching a specific blood type (e.g. the square port is blood type B−). Thus, the chance of fatal error by providing mismatched blood is still high unless a consistent use or method is established wherein one type of port is used for one type of blood. Such a method is not taught.

Moreover, the variously configured structures of each port cause serious practical disadvantages to arise during use. Various mating configurations require that a multitude of pairs of parts be manufactured, and ultimately stored by the healthcare provider. Thus, depending on the frequency of need or if a sudden "run" on a particular blood type occurs, a mating part (the spike and attached infusion cannula) may become temporarily unavailable despite the availability of blood type and properly coded bag. Thus, to prepare for such contingencies, the provider must store an overabundance of each of the mating parts (cannulas having differently spiked ends) leading to unnecessary and increased costs. In an environment having limited storage space considerations, such as ambulances, such stock piling is highly impractical. Furthermore, the presence of multiple parts require added time to locate the properly stored part, such time often being unavailable to a health care provider in emergency situations.

The present invention provides a means by which all of these problems are overcome, the inherent structure of such means obviating the need to have excess storage for multiple parts and most importantly, preventing the inadvertent cross-matching of different blood types. None of the above inventions and patents, taken either singly or in combination, is seen to describe the instant invention as claimed.

SUMMARY OF THE INVENTION

The present invention relates to an apparatus to prevent accidental transfusion of mismatched blood types from a blood bag containing pre-typed blood to a patient of a different blood type. The system includes two major independent but mating components: 1) a cannula spike attached to a cannula adapted for intravenous infusion of a fluid from the bag into a patient and 2) a plurality of at least four different individual receptacle ports of graduated size, of which at least one is selectively attached to the outside of pilot tube at the time of blood typing.

The cannula spike is a connected series of decreasingly sized individual cannula spike units, each unit being configured to be matingly received by and uniquely coded to its matching female receptacle port. Each of the units is individually removable from the cannula spike to allow a user to cannulate a patient according to blood type and then correctly choose the unit matching the blood bag. A connection between mismatched blood bag and cannula is thus prevented. Each unit may also be color coded according to a universal color coding system for blood, bar coded particularly between patient and cannula, and affixed with printed, embossed, raised or other linear indicia to further assist the user in avoiding an accidental mismatch between blood types.

Accordingly, it is a principal object of the invention to provide a blood bag port and cannulation system which virtually eliminates the chance that a mismatched blood type will be infused into a patient.

It is another object of the invention to provide a blood bag port and cannulation system which are matingly configured.

It is a further object of the invention to provide a mating cannula spike which is connected in series to other cannula spikes of differing sizes as a separable but single unit.

Still another object of the invention is to provide a blood bag port and cannulation system having visual indicia coding the mating port with the cannula spike.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is an apparatus to prevent accidental transfusion of mismatched blood types from a blood bag containing pre-typed blood to a patient. Referring to the drawings for a general discussion of the system and its use and first to FIG. 1, a standard blood bag B having a pilot tube T is shown to which the present mating port and cannulation system 10 has been attached. Each such pilot tube T includes a standard fluid impermeable diaphragm D, shown in a representational manner in FIG. 2, which is easily punctured when the fluid is to be released by an appropriately sharpened piercing member. Filters and any other components which may also come as a standard part of the blood bag are not shown in FIG. 2, but should be understood to be included as necessary in order to implement a complete system for providing blood or other bodily fluids to a patient by accepted medical procedures.

The system 10 includes two major independent but mating components: 1) a cannula spike 20 attached to a cannula 600 adapted for intravenous infusion of a fluid from the bag B into a patient (not shown) and 2) a plurality of at least four different individual receptacle ports 50 of graduated size, of which plurality an appropriate one is selected and attached to the outside of pilot tube T at the time of blood typing.

The cannula spike 20 is a connected series of decreasingly sized individual cannula spike units 22, each unit 22 being configured to be matingly received by and uniquely coded to its matching female receptacle port 50. The series of graduated units 22 comprising the cannula spike 20 begins with a first unit 24 and ends with a last unit 26 connected to a cannula 600 leading to the patient (not shown). As suggested by the variously sized cannula spikes 20 shown in broken lines in FIG. 1, each of the units 22 is individually removable from the cannula spike 20. The last unit 26 may be affixed permanently to the cannula 600 or be adapted to receive a standard male member of commercially available flexible tubing cannulas as presently commonly used throughout the medical industry. Each of the cannula spikes would preferably come packaged in an appropriate sterile package for use with sterile procedures, which may include a cap (not shown) covering the first unit 24.

Figure 1:
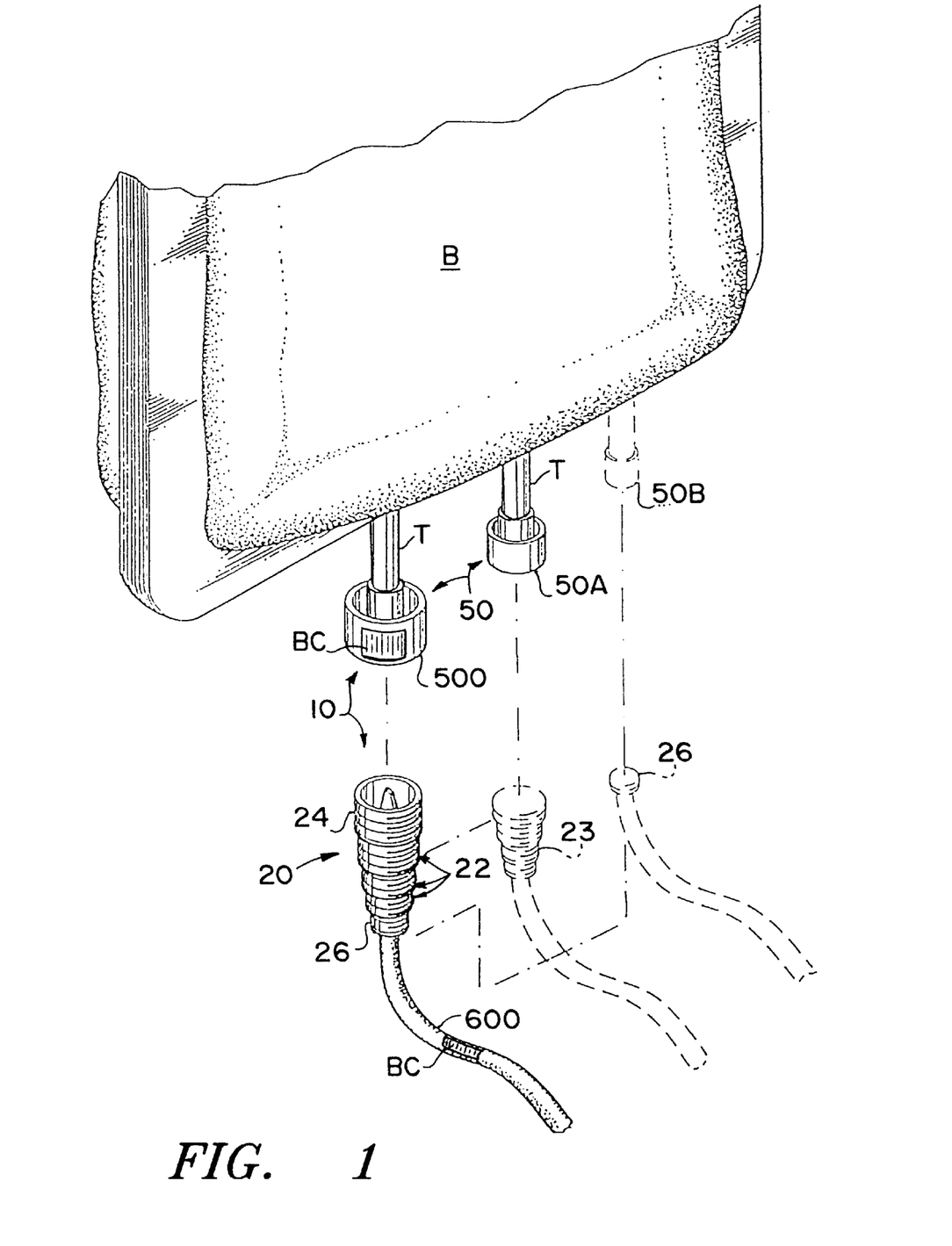
FIG. 1 is a fragmented environmental, perspective view of the mating port and cannulation system on a blood bag.

As suggested by cannula spikes 23 and 26 shown in broken lines in FIG. 1, in order to permit the proper mating unit 22 to be chosen for mating with a given port 50, the user must simply remove and may discard the inappropriately sized units 22. For example, comparing a complete cannula spike 20 with a modified cannula spike 26, it is readily apparent that all units 22 have been removed except the last unit 26 for adaptation to port 50B. As is further apparent, the last unit 26, which comprises a modified cannula spike, is substantially smaller in diameter than either port 500 or 50A, and therefore is incapable of being securely received by either such port 500,50A.

Moreover, as suggested in FIG. 1 by the plurality of ports 50,50 shown, each port 50 is an individual unit, graduated in size to mate with only one size cannula spike unit 22. Each different size is also given an indicia corresponding to a different blood type, as will be discussed in more detail below relative to FIG. 6. For example and for ease of discussion, the preferred embodiment of the system 10 will be discussed as having four ports of different sizes corresponding with the four blood types A, B, AB and O; however, it should be understood that variations on the preferred embodiment are possible in which more than four differently graduated port sizes are provided. One such possible embodiment would include eight graduated sizes to correspond to the various combinations of typing attributable to both the four blood types as well as the two rh-factors.

Therefore, preferably at the time of typing the blood, a corresponding port 50 is attached to the pilot tube T of the blood bag B to properly identify its contents as either O, A, B, or AB, typed blood. Each port 50 is identified by visual indicia corresponding to each individual blood type, applied in a standardized manner wherein each differently sized port 50 is associated with a different blood type. All ports 50 of the same size are designated by the same blood type, e.g. port 50A is associated with AB blood type. In order to accommodate universal recipients (i.e. AB typed patients), a second pilot tube T is provided having receptacle port 50A corresponding to the mating unit 22 having been identified as AB. Thus, any blood typed bag having a first port 500 corresponding to non-AB typed blood contents will also be provided with a second port 50A for receipt by AB typed patients. A third port 50B may be further provided as a receiver for the last unit 26, which identifies no specific blood type, but which serves only as a mating port and unit for quick or emergency attachment of a cannula to a bag.

Preferably, the cannula spike 20 is sequenced from the first unit 24 to the last unit 26 such that the first unit 24 corresponds to O typed blood and is so labelled; the next smaller unit 22 is A; the next smaller unit 22 is B; the next smaller unit is AB; and the last unit 26 is a non-typed universal unit which mates with port 50B. Obviously, if rh-factors are typed, interposingly graduated units 22 are added to provide for a positive and negative blood type, thus doubling the number of typed units 22 and typed ports 50.

Figure 2:
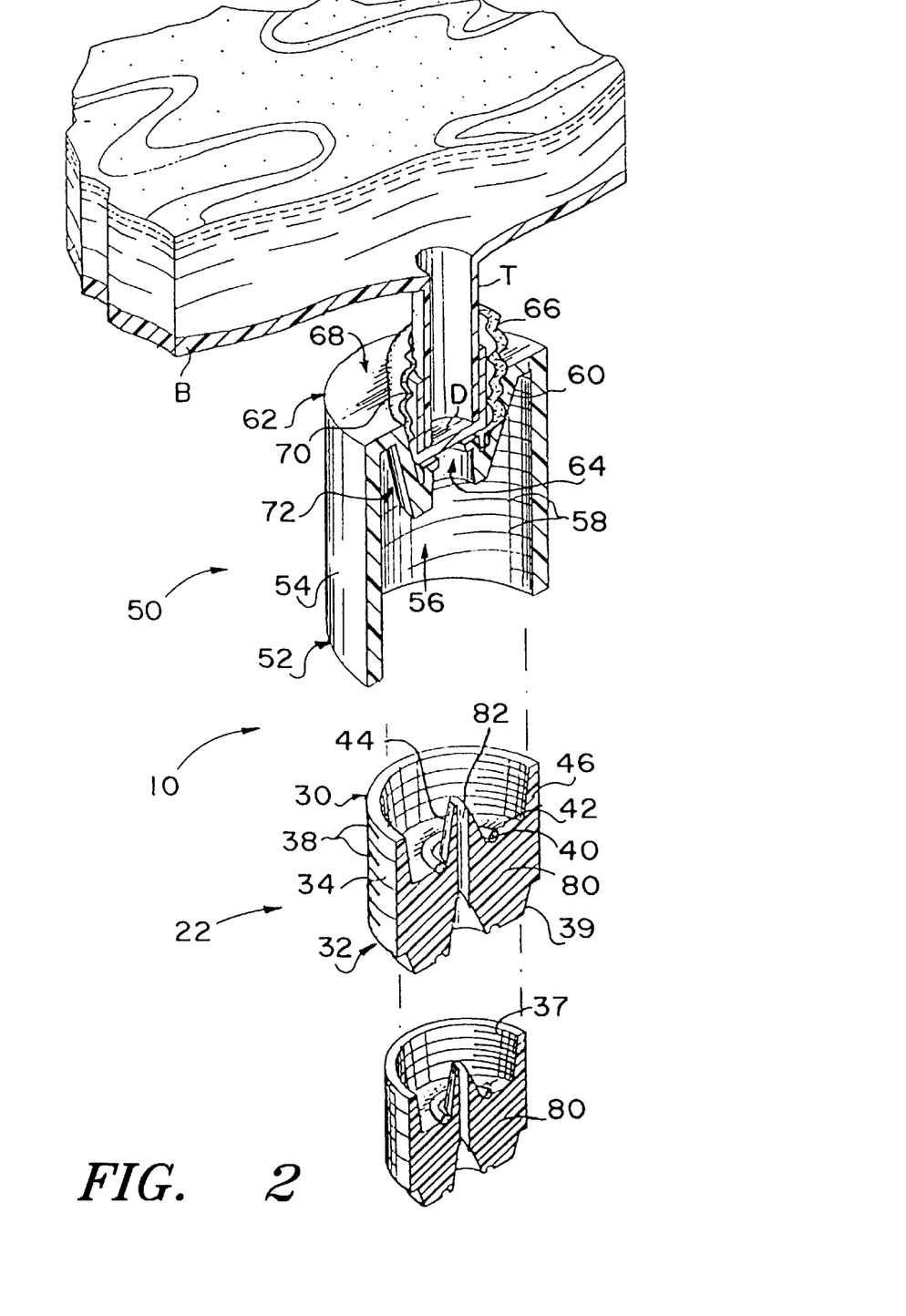
FIG. 2 is a perspective, partial sectional view of a first embodiment of the mating port and cannulation system attached to a pilot tube of a blood bag.

Now referring to FIG. 2 for discussion of the specific structure of each component in the system 10, each different port 50 defines a receiving chamber 56 having a different diameter for receiving a mating unit 22. A mating pair, comprising a port 50 and a unit 22, is thereby defined. Each port 50 is a modified tube having a wall 54 circumscribing a predetermined internal diameter according to a standardized set of diameters, each different diameter corresponding to a different blood type. The set of standardized tube diameters is graduated in dimension from a largest size, defined by the outer diameter of the first unit 24 of the cannula spike 20, to a smallest size, defined by the outer diameter of the last unit 26. Each unit 22 of the cannula spike 20 also has an annular wall portion 46 of uniform thickness. It should be apparent that a unit 22 of a size larger than its mating port 50 is incapable of entering chamber 56 and thus prevented from making a connection despite the most persistent of efforts.

The tube at the lower edge 52 of wall 54 is open ended to receive its mating unit 22. The tube wall 54 at the upper edge 62 is integrally capped by an end cap 68 which defines a through bore 64 generally corresponding in diameter to the pilot tube T. A sleeve 66 made of a flexible material with a highly resilient memory, such as latex or synthetic rubber, is permanently attached to the end cap 68 and circumscribes the through bore 64, and may be so attached by embedding the sleeve 66 into the end cap 68 during a molding process. The sleeve 66 is tubular and has an inner diameter less than the outer diameter of the pilot tube T so as to closely and frictionally seat over the outside of the pilot tube T, thereby creating an air-tight seal. This allows the port 50 to be snugly retrofitted to the end of a pilot tube T. Thus, the sleeve 66 may be rolled or stretched over the pilot tube T and, upon release, the sleeve 66, attempting to return to its resting configuration, snugly grips the pilot tube T. The sleeve may be additionally provided with internally disposed circumferential ridges 70 for enhancing frictional engagement with the pilot tube outer wall. Thus, the end cap 68 is sealed to the pilot tube T by means of the sleeve 66 so that the pilot tube T and the through bore 64 align. Other sealing means suitable for attaching the end cap 68 over the diaphragm D to a blood bag, whether having a pilot tube or not, can be envisioned which allow the use of the safety features of the present invention to be fully realized. Therefore, it should be apparent that the sleeve 66 is intended to be exemplary and not limiting.

The end cap 68 is further configured to provide that the through bore 64 is concentrically received upon the diaphragm D of the pilot tube T allowing its puncture by means of a spike 44 of the mating unit 22. A frusto-conical bore wall 60 depends from the end cap 68 inward into the receiving chamber 56 and defines the through bore 64. To allow passage of the hollow spike 44 of unit 22, the through bore 64 should have a diameter of no less than that of the maximum diameter of the hollow spike 44 on unit 22, thereby allowing complete passage of the spike 44. The end cap 68 has an exterior surface which is integral with the exterior surface of the frusto-conically configured bore wall 60, the bore wall 60 defining an inwardly recessed pocket (not numbered) which allows the diaphragm D of the pilot tube T to reside below the plane of the interior surface of end cap 68. The pocket therefore permits the diaphragm D to reside next to the through bore 64 for penetration by the hollow spike 44 of a mating unit 22 passing through the through bore 64, yet also permits the spike 44 to be shorter than the surrounding annular wall portion 46 of the unit 22, the wall thereby serving as a safety guard to aid in preventing inadvertent skin punctures by a user.

It is further noted that in bags having filters internally disposed in the pilot tube, the dimensions of the configuration as described herein should be modified so that the penetration of the hollow spike 44 under no circumstance interferes with the function of the filter.

It is apparent from the Figures that a unit 22 which is smaller than a mating unit of port 50 is permitted to pass into chamber 56. However, the bore wall 60 prevents the inadvertent puncture of diaphragm D by the hollow spike 44 due to the non-mating juxtaposition of the frusto-conically configured bore wall 60 within the proportionally smaller inner diameter of the annular wall portion 46 of a non-mating unit 22. As can be observed from FIG. 2, the bore wall 60 and tube wall 54 defines a receiving well 72 for receiving the annular wall portion 46 encircling hollow spike 44 of unit 22. The annular wall portion 46 has a height at least equal to the height of the spike 44 and the well 72 is equal in depth to that of the height of the annular wall portion 46. This relationship allows the annular wall 46 to nest within the well 72 and permits a mating spike 44 to pass through the through bore 64 and puncture the diaphragm D. However, the inclined bore wall 60 will not allow penetration of the diaphragm D by a smaller sized unit 22 because the wall portion 46 will ride onto and abut the bore wall 60 before fully nesting, thus preventing the spike 44 from penetrating far enough into the through bore 64 to puncture the diaphragm D. In other words, should the smaller unit 22 be inserted into chamber 56, the upper edge (at 30) of the annular wall 46 would come into contact with the frusto-conically inclined wall 60 prior to contact of the spike 44 with diaphragm D. Because the smaller unit 22 is limited by its decreased internal diameter, the smaller annular wall cannot nest fully within well 72.

In the preferred embodiment as shown in FIG. 2, the internal wall of the port 50 and the external wall 34 of the unit 22 are each matingly threaded to receive one another. Mating threads are schematically represented at 58 and 38. Likewise, each unit 22 is provided with an externally disposed thread 39 which is mated with an internally disposed thread 37 on the inside surface of annular wall 46.

In the preferred configuration of each unit 22, each unit 22 is provided with a body 80 having a spiked end portion 30 and an opposite end portion 32. The spiked end portion 30 includes the hollow spike 44 defining a concentric, continuous bore 82 passing through the longitudinal axis of the body 80. The spiked end portion 30 of one unit 22 is adapted to be removably attached with an opposite end portion 32 of an adjacent and differently sized unit 22. Therefore, each unit 22 is further adapted to be fittingly mated to an opposite end portion 32 of the prior unit 22, in addition to being fittingly mated to an associated port 50. Thus, a graduated array defining the cannula spike 20 can be assembled which defines a continuous through-bore from the first unit 24 to the last unit 26, with each spiked end portion 30 nesting over the opposite end portion 32 of the prior unit 22. As a guard against passage of air between the walls of each unit 22, a resilient sealing ring, such as a rubber or synthetic resilient plastic O-ring 40, may be provided between the seating surface 42 of the unit 22 and the frusto-conical wall 60. Such O-ring 40 may be omitted where it is determined through experimentation to be unnecessary in light of the suitability of materials for use as the body of each component to adequately prevent passage of fluids and air.

Figure 3:
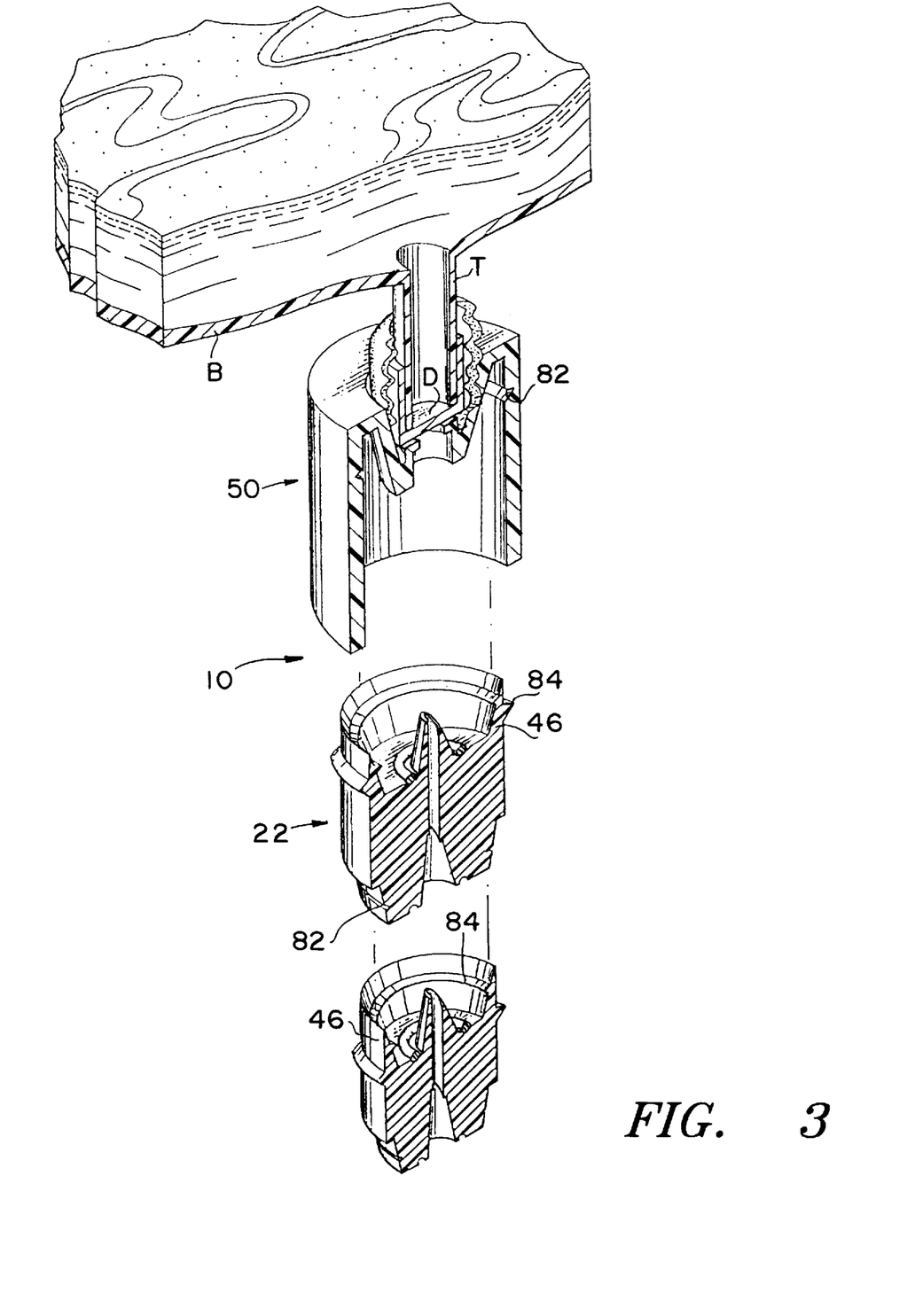
FIG. 3 is a perspective, partial sectional view of second embodiment of the mating port and cannulation system attached to a pilot tube of a blood bag.
Figure 4:
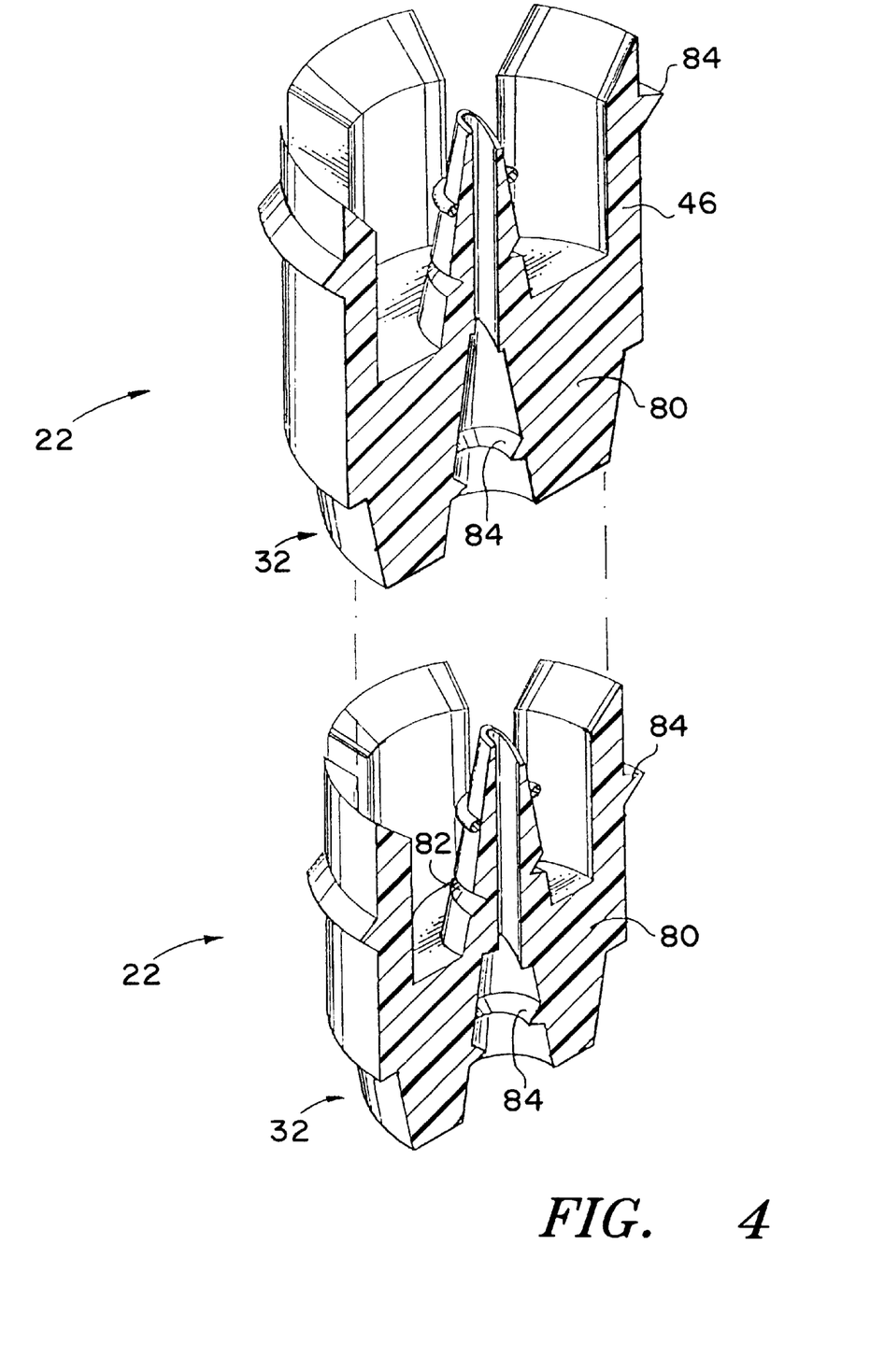
FIG. 4 is a sectional perspective view of two of the spike components of the second embodiment.

In alternative embodiments, as shown in FIG. 3 and FIG. 4, the mating walls of each unit 22 and port 50 are shown has having a receiving groove 82 which receives a resilient tooth 84 or ridge which is disposed on the outer surface of the annular wall 46 in lieu of threads. FIG. 4 shows that the annular wall 46 may be segmented to allow the wall of a unit 22 manufactured of a suitably resilient material, such as some plastics, to resiliently flex to more easily engage the groove 82 of port 50. Moreover, the receiving groove 82 of each unit 22 may be located on spiked tooth 44 for engagement with a resilient ridge 84 disposed within mating configuration of the body 80 at the opposite end portion 32. Such configurations allow the component units 22 or mating pair 50,22 to snap fit with one another.

In FIG. 5 a final embodiment of the cannula spike 20 is shown wherein the series of graduated units 22 are an integrally molded plastic unit having the continuous bore 82 defined by an internal tube 86. The internal tube 86 is supported by a plurality of rigid septa 88, each septum 88 perpendicularly attached between the internal tube 86 and the unit body 80, defined by a tubular wall 80. The septa 88 thereby support the internal tube 86 in a coaxial relationship to the tubular wall 80. Both the tubular wall 80 and the internal tube 86 are scored for breakage along score grooves 90. Each score grove 90 is positioned approximately equidistant between septa 88,88 on both the internal tube 86 and the tubular wall 80 and on the same transverse plane. The septa 88 are exemplary and other spoke or arm support systems can be envisioned which fulfill the purpose of the septa.

The material of manufacture of the cannula spike 20 should be chosen having a quality such that a score groove of sufficient depth provides a perfectly clean break without loss of particulate matter from the tubular wall. Moreover, the material may be chosen to frangible along the score line, yet rigid having a shape retaining memory to prevent deformation of the body of the unit inconsistent with the mating aspects of the present invention. Many plastics are known to have such qualities and the material may be chosen from such group. Moreover, the score groove 90 on the internal tube 86 should circumscribe the tube at such angle so as to define an elliptical cross section and thereby provide the internal tube 86 with a tapered spike for puncture of the diaphragm when broken.

In addition to being sized differently to correspond with different blood types, the present invention 10 is provided with additional visual indicia to correspond with each of the different blood types. A first type of indicia is a bar code, which may be applied by known labelling techniques to each mating port 50 and cannulation unit (cannula spike 20 and cannula 600) for further automated identification and optical reading of the bag's contents to match a patient's blood type. More specifically, matching bar codes should be applied both to a patient (by bracelet, associated patient medical chart, or other means), as well as, to any integral component of the cannulation unit 20,600 by a tag, label, printing method or other suitable labelling means.

By including bar coding to link patient with cannulation unit, the present invention virtually eliminates human error between the endpoints of typing the blood and typing the patient. Each component of the present invention 10 can only be linked with another if matching, physical parameters are present. In other words, a properly typed patient becomes linked by bar code to the cannulation unit 20,600, which in turn is physically limited in size to a properly chosen mating port 50 by virtue of its mating unit 22. Unit 22, if improperly chosen, cannot fit a properly chosen blood typed bag having mating port 50. Unit 22, if properly chosen, cannot fit an improperly chosen blood typed bag.

Such linking is of particular importance in situations in which autologous information is critical, such as in plasmapheresis, wherein the patient must receive his or her own blood components. Although not absolutely necessary in most situations where a blood type match is adequate, in situations wherein autologous information is important to a medical procedure, the mating port 50 must also be labelled by a third bar code matching the bar code associated with both the patient and cannulation system. Bar coding of the mating port 50 or the blood bag may therefore be added as a feature of the present invention.

Other visual indicia are also included. As shown in FIG. 6, various visual indicia are represented on each matching component. A first indicia 92, preferably indicia embossed or molded into the body of each port 50 and unit 22, is irremovably applied in order to permanently identify each mating port 50 and unit 22 according to its predetermined blood type. Other means may be used, such as printed labelling. The embossed or raised indicia 92 is applied to a mating pair of port 50 and unit 22a, such that each port and unit pair 50,22a receives an identical pair of raised indicia.

Each such pair of raised indicia identifies each one of the at least four blood types chosen from the group consisting of A, B, AB, and O, and preferably positive and negative rh-factors as well. FIG. 6 illustrates two units, 22a and 22b, having indicia 92 of the same blood type (O), but of different rh-factors (O− and O+). The port 50 is also labelled with embossed indicia 92, shown as O+. As previously noted, the rh-factor is not necessarily harmful to a patient, and if the appropriate rh-factored blood type is not available, an oppositely signed but matching blood type may often be given without consequence. Hence, as suggested in FIG. 6, both units 22a,22b are designated as blood type O and are thus sized the same, with both being configured in size to be capable of mating with port 50.

However, the alternative embodiment provides that, because the units 22 are identified by oppositely signed rh-factors, each unit 22a and 22b are further differentiated and prevented from interacting with a non-matching port by providing a right-hand thread or left-hand thread assigned in a standard manner to either the positive or negative rh-factor. As also shown in FIG. 6, the units 22a,22b are shown having threads of opposite windings, unit 22a with a schematically represented left-hand thread 38a and unit 22b showing a right-hand thread 38b. Port 50 has a left-hand thread 58, thus capable of mating with the right-hand thread of unit 22a and opposing the left-hand thread of unit 22b. Clearly, an attempt to connect unit 22b with port 50 would be prevented.

Each mating pair of a port 50 and a unit 22 may also be provided with additional coding features, such as colored plastic bodies of the port 50 and unit 22 being the same hue (either opaquely or transparently colored), wherein each hue is visually distinct for each different said mating pair 50,22. One visually distinct hue is chosen to represent a different one of each of the at least four blood types chosen from the group consisting of A, B, AB, and O, and rh-factors.

Although a standardized color coding system for blood types is generally known and used in the medical field, the use of transparently colored bodies to code unit 22 and port 50 for blood type is unknown and confers an added advantage when combined with a final visual indicia for warning that an incorrect rh-factor match has occurred, particularly when applied in an embodiment of the present invention which does not utilize opposingly threaded components. The final visual indicia comprises opposite diagonal or opposingly spiralling lines applied to the port 50 and body 22, and chosen to represent either a positive or a negative rh-factor.

As shown in FIG. 6, each diagonal or spiralling line 94 is unidirectional when representing the same rh-factors and opposingly directional when representing different rh-factors. The lines are unidirectionally applied to a mating pair, such as port 50 and unit 22a. Such lines would also correspond to the direction of the thread if the components were to include a thread corresponding to rh-factors as described above. Such linear indicia are chosen to extend in two diagonally opposing directions wherein each one of the lines consistently identifies a different one of two rh-factors.

Referring still to FIG. 6, a positive rh-factor is identified by a schematically represented counter-clockwise spiral line 94 wrapping around the port 50 beginning at the lower edge 52 of the port 50 and spiralling counter-clockwise in a plurality of turns upwards to its upper edge 62 (similar to a barber shop pole). A unit 22a identifying a positive rh-factor is provided with a similar spiralling counter-clockwise line 94a extending from the first or opposite end portion 32 to the spiked end portion 30 of the unit 22. However, negative rh-factors would be identified by clockwise spiralling lines, such as identified on body 22b as clockwise line 94b.

When both the port 50 and unit 22 are manufactured of transparent or translucent materials, and a port and unit of differently identified rh-factors are mated or nested, the spiralling lines 94,94b provide the appearance that they cross to form a plurality of "X"s. Moreover, even if the components are opaque, when a positive port 50 and an negative unit 22b are viewed, the lines will appear to be spiralling in opposite directions. However, when a correctly mated pair 50,22a is viewed together, the spiralling lines will appear to be spiralling in the same clockwise direction and can be viewed in parallel relation through the mating transparent bodies of port 50 and unit 22a. Likewise, if the bodies are transparently colored, as alluded to above, the hue of the overlapping or nesting bodies would become altered, causing a different hue to appear and alerting a healthcare provider that an rh-factor mismatch is present. Nevertheless, because emergency procedure may dictate that such a mismatch is acceptable under the circumstances, the blood flow may take place despite the rh-factor mismatch.

It is to be understood that the present invention is not limited to the embodiments described above, but encompasses any and all embodiments within the scope of the following claims.

I claim:

1. A mating port and cannulation system for use with storage bags including a fluid impermeable diaphragm, comprising:

a cannula spike comprising a plurality of separable units, said plurality of separable units being an array of units graduated in size from a largest size defined by a first unit to a smallest size defined by a last unit, each said unit having a body, having a spiked end portion and an opposite end portion, and defining a through bore for passing a fluid therebetween, said spiked end portion including a hollow spike in communication with said through bore, said spiked end portion being adapted to be removably and sealedly attached to a said opposite end portion of a prior graduated unit of said array, said opposite end portion of said last unit being adapted to attach to a cannula for infusion of fluids, wherein each said unit is matingly and separably connected to define a continuous channel formed of each said through bore and thereby being in serial communication with another from said first unit to said last unit of said array;

a port defining a receptacle for sealedly receiving said spiked end portion of only one of said units of said array, said port further defining a passage from said receptacle, and including a sealing means for attaching said port over said diaphragm and placing said passage in communication with the diaphragm, whereby a mating pair comprising the port and one unit is defined; and raised indicia applied to said mating pair of said port and said unit, wherein each said port and said unit of said mating pair receives an identical said raised indicia, wherein further said raised indicia is different for each different mating pair, wherein further each said different raised indicia identifies each of at least four blood types chosen from the group consisting of A, B, AB, and O.

2. The system according to claim 1, wherein each said different raised indicia further identifies a different one of two rh-factors.

3. The system according to claim 1, including a linear indicia applied to a mating pair of said port and said unit, wherein each said port and said unit of said mating pair receives an identical linear indicia, wherein further said linear indicia is chosen from the group consisting of lines extending in two diagonally opposing directions, each one of said lines consistently identifying a different one of two rh-factors, whereby different rh-factors are identified by said port and said unit when two diagonal lines are opposingly aligned.

4. The system according to claim 1, wherein a mating pair of said port and said unit is matingly threaded to receive one another.

5. The system according to claim 1, wherein a mating pair of said port and said unit is provided with resiliently flexible means for joining one another.

6. The system according to claim 1, wherein said cannula spike is integrally formed having score lines between each said unit for breaking and separating units from said cannula spike.

7. The system according to claim 1, wherein said cannula spike is labelled by a bar code and further including a patient labelling means having the same said bar code.

8. The system according to claim 7, wherein said patient labelling means is a bracelet.

9. A mating port and cannulation system for use with storage bags having a pilot tube including a fluid impermeable diaphragm, comprising:

a plurality of receptacle ports for receiving a cannula spike, each of said plurality of receptacle ports being a tube having a different internal diameter thereby defining a largest diameter and a smallest diameter, each said port being adapted to attach to the pilot tube;

a cannula spike comprising a plurality of mating units, each unit of said plurality of mating units being of graduated size from a largest size defined by a first unit to a smallest size defined by a last unit, each unit being matingly connected to an adjacent unit in a graduated array and further defining a continuous through-bore from said first unit to said last unit, each said unit having a body having a spiked end portion and an opposite end portion, said spiked end portion including a hollow spike defining said through bore in part, said spiked end portion of said first unit adapted to be removably attached with the one of said plurality of receptacle ports having said largest diameter, said spiked end portion of each subsequent unit being further adapted to be fittingly mated to said opposite end portion of an adjacent unit, said spiked end portion being further adapted to be removably attached to a different one of said each of said plurality of receptacle ports, and said opposite end portion of said last unit being adapted to attach to a cannula for intravenous infusion, whereby a mating pair is selectively defined between one said unit and one said port, and, one said unit and one opposite end portion;

wherein said mating pair of said port and said unit is colored in the same hue, wherein each said same hue is visually distinct for each different said mating pair, and wherein further a different visually distinct hue is chosen to represent each of at least four blood types chosen from the group consisting of A, B, AB, and O.

10. The system according to claim 9, wherein each said visually distinct different hue further identifies a different one of two rh-factors associated with each of the at least four blood types chosen from the group consisting of A, B, AB, and O.

11. A mating port and cannulation system combination with storage bags having a pilot tube including a fluid impermeable diaphragm, comprising:

a plurality of receptacles having an internal diameter chosen from a group consisting of at least four different diameters, thereby defining a largest diameter receptacle and a smallest diameter receptacle, each said receptacle of a different diameter having identifying means for visually associating a different one of four blood types chosen from the group consisting of A, B, AB, and O, a selected one of said plurality of receptacles attached to said pilot tube;

air-tight attachment means connecting said selected one receptacle to the pilot tube; and, a cannula spike comprising a plurality of separable units, said plurality of separable units being an array of units graduated in size from a largest size defined by a first unit to a smallest size defined by a last unit, each said unit having a body, having a spiked end portion and an opposite end portion, and defining a through bore for passing a fluid therebetween, said spiked end portion including a hollow spike in communication with said through bore, said spiked end portion being adapted to be removably and sealedly attached to a said opposite end portion of a prior graduated unit of said array, said opposite end portion of said last unit being adapted to attach to a cannula for infusion of fluids;

wherein each said unit is matingly and separably connected to define a continuous channel formed of each said through bore being in serial communication with another from said first unit to said last unit of said array;

wherein further said first unit is adapted to sealedly mate with said largest diameter receptacle, said last unit is adapted to sealedly mate with said smallest diameter receptacle and each of said graduated units is adapted to sealedly mate with a different one of the remaining receptacles, each thereby defining a different mating pair; and wherein said hollow spike is sized to puncture said diaphragm of said pilot tube only when a mating pair is joined.

* * * * *